(12) United States Patent
Marsais et al.

(10) Patent No.: US 7,728,170 B2
(45) Date of Patent: Jun. 1, 2010

(54) METHOD FOR PREPARING A POLYCARBOXYLIC COMPOSITION COMPRISING AN ELECTROCHEMICAL OXIDATION STAGE OF A MONOSACCHARIDE COMPOSITION

(75) Inventors: Francis Marsais, Rouen (FR); Christian Feasson, Bihorel les Rouen (FR); Guy Queguiner, Bihorel les Rouen (FR); Mathias Ibert, Rouen (FR); Serge Comini, La Gorgue (FR); Jean-Marc Grossel, Merville (FR)

(73) Assignee: Roquette Freres, Lestrem (FR)

( * ) Notice: Subject to any disclaimer, the term of this patent is extended or adjusted under 35 U.S.C. 154(b) by 1475 days.

(21) Appl. No.: 10/528,356

(22) PCT Filed: Sep. 12, 2003

(86) PCT No.: PCT/FR03/02702

§ 371 (c)(1),
(2), (4) Date: Mar. 18, 2005

(87) PCT Pub. No.: WO2004/027118

PCT Pub. Date: Apr. 1, 2004

(65) Prior Publication Data
US 2005/0252785 A1 Nov. 17, 2005

(30) Foreign Application Priority Data
Sep. 18, 2002 (FR) .................................. 02 11546

(51) Int. Cl.
C25B 3/02 (2006.01)
(52) U.S. Cl. .................................... 562/590; 562/512.4
(58) Field of Classification Search ........................ None
See application file for complete search history.

(56) References Cited

U.S. PATENT DOCUMENTS

| 5,413,819 A | 5/1995 | Drs |
| 5,567,236 A | 10/1996 | Schapira et al. |
| 5,831,043 A | 11/1998 | Fleche |
| 5,981,742 A | 11/1999 | Fleche |

FOREIGN PATENT DOCUMENTS

| EP | 0 656 051 B1 | 6/1995 |
| EP | 0 650 941 B1 | 3/1997 |
| EP | 0 605 318 B1 | 4/1997 |
| EP | 0 780 399 A2 | 6/1997 |
| EP | 0 798 310 A1 | 10/1997 |
| EP | 0 595 266 B1 | 1/1999 |
| EP | 0 972 825 A2 | 1/2000 |
| EP | 1 027 931 | 8/2000 |
| EP | 1 027 931 A1 | 8/2000 |
| FR | 715 176 | 11/1931 |
| FR | 2 657 601 | 8/1991 |
| FR | 2 735 788 | 12/1996 |
| WO | WO 91/00901 | 1/1991 |
| WO | WO 91 04988 | 4/1991 |
| WO | WO 95/02614 | 1/2005 |

OTHER PUBLICATIONS

Abstract of Journal of Chromatography, A 1994, 676(2), 461-468.*
Abstract of Ultrasonics Sonochemistry 1995, 2(2) s105-s109.*
Francois et al., "TEMPO-mediated oxidation of maltodextrins and D-glucose: effect of pH on the selectivity and sequestering ability of the resulting polycarboxylates", Carbohydrate Research, 330, 2001, pp. 21-29.
Ito et al., "Catalytic Oxidation of Sugars by 4-(Acetylamino)-tempo", Proc. Electrochem. Soc. 1993, vol. 93, 11, pp. 260-267.
Schnatbaum et al., "Electroorganic Synthesis 66: Selective Anodic Oxidation of Carbohydrates Mediated by TEMPO", Synthesis, 1999, No. 5, pp. 864-872.
Ibert et al., "Determination of the side-products formed during the nitroxide-mediated bleach oxidation of glucose to glucaric acid", Carbohydrate Research, 337, 2002, pp. 1059-1063.

* cited by examiner

*Primary Examiner*—Daniel M Sullivan
*Assistant Examiner*—Yevegeny Valenrod
(74) *Attorney, Agent, or Firm*—Young & Thompson

(57) ABSTRACT

A method for preparing a polycarboxylic composition, includes a stage in which a monosaccharide composition undergoes an electrochemical oxidation treatment carried out in the absence of sodium hypochlorite and in the presence of a) an amine oxide and b) a carbon-based anode. Preferably, the anode is selected from the group comprising carbon felt and granular active carbon. The electrochemical oxidation treatment can be carried out advantageously at a pH, preferably of between 11.5 and 14. The method makes it possible to obtain novel products, especially 2-carboxy-2, 3, 4-trihydroxypentane-dioicious acid, the salts and derivatives thereof.

10 Claims, No Drawings

METHOD FOR PREPARING A POLYCARBOXYLIC COMPOSITION COMPRISING AN ELECTROCHEMICAL OXIDATION STAGE OF A MONOSACCHARIDE COMPOSITION

This is a 371 National Stage application of International application no. PCT/FR2003/02702, filed Sep. 12, 2003, which claims priority to French application no. 02/11546, filed Sep. 18, 2002. The entire contents of the above-referenced applications are hereby incorporated by reference in their entirety.

FIELD OF THE INVENTION

A subject-matter of the present invention is a novel method for preparing polycarboxylic compositions, said method comprising a stage of electrochemical oxidation of a monosaccharide composition carried out under specific conditions.

It also relates, as novel materials, to some of the polycarboxylic compositions that are obtained by said method.

In addition, the present invention is directed to the use of said polycarboxylic compositions in certain industries, such as, for example, those of detergents and cleaning agents, of water treatment or of hydraulic binders or the food or pharmaceutical industries.

BACKGROUND OF THE INVENTION

In those industries, it is common to use materials resulting from products of natural or synthetic origin which are of polymeric or monomeric structure and which comprise at least two carboxylic functional groups. All or part of these functional groups can exist in either the "free acid" (COOH) form or other forms, in particular in the form of associated salts, such as alkali metal or alkaline earth metal salts. These materials, which can be described as "polycarboxylates", can be used in particular as chelating or sequestering agents for metals, detergency builders or cobuilders, or agents which delay the setting of hydraulic binders but also as stabilizing, structuring, dispersing, disintegrating or stripping agents for compositions of any nature and destination.

They can consist of natural products derivatives, such as poly- and monosaccharides, in particular of starch derivatives or of starch-hydrolyzed products.

They can be, inter alia:

carboxyalkylated derivatives of starch hydrolysates, glucuronyl-arabinarates or glucuronyl-glucarates, obtained from starch hydrolysates, glucuronyl-glucaric acid, glucaric acid or mannaric acid, obtained respectively from maltitol, sorbitol or mannitol, the preparation and the uses of such polycarboxylates resulting from natural products being disclosed in particular in patents WO 95/02614, EP 780 399 and EP 798 310 on behalf of the Applicant Company and, for example, in patent EP 656 051.

Other monomeric or polymeric polycarboxylates result from products of synthetic or natural origin that are of non-saccharide nature, such as, for example:

dicarboxylic acids, such as tartaric acid, succinic acid or glutaric acid, tricarboxylic acids, such as citric acid or nitrilotriacetic acid ("NTA"), tetracarboxylic acids, such as ethylenediamine-tetraacetic acid ("EDTA"), (co) polymers of ethylenic carboxylic acids, such as, for example, polyacrylates, the uses of such polycarboxylates resulting from products of non-saccharide nature being, inter alia, disclosed in patents FR 2 657 601, FR 2 735 788, WO 91/00901, EP 565 266, EP 605 318, EP 650 941 or EP 972 825.

In view of the current restrictions for the protection of the human life and the environment, it is advisable to have available polycarboxylates resulting from renewable products of natural origin.

For approximately a decade, numerous studies have focused on several polycarboxylates such as glucaric acid and its salts.

The abovementioned patent EP 656 051 discloses the preparation of phosphate-free detergents based on zeolites and/or on lamellar silicates comprising, as complexing agents, polyhydroxydicarboxylic acids or polyhydroxydicarboxylic acid salts comprising from 4 to 6 carbon atoms and at least 2 hydroxyl groups per molecule, such as, in particular, sodium glucarate and sodium galactarate.

The abovementioned patent EP 798 310, published on behalf of the Applicant Company, discloses, in its Example 1, the preparation of a composition comprising 33% of glucaric acid in the form of its sodium salt and 67% of sodium chloride, with the absence of products from the overoxidation of glucaric acid. This composition, which has high content of NaCl, is obtained by oxidation of sorbitol by sodium hypochlorite (NaOCl or "bleach") in the presence of a catalyst composed of a binary or tertiary alkyl nitroxy, such as 2,2,6,6-tetramethylpiperidinyloxy or "TEMPO".

More recently, other studies have been described in the paper by J. F. Thaburet et al. entitled "TEMPO-mediated oxidation of maltodextrins and D-glucose: effect of pH on the selectivity and sequestering ability of the resulting polycarboxylates", Carbohydrate Research, 330 (2001), pp. 21-29.

These studies have shown that the oxidation of glucose or sorbitol in the presence of TEMPO and NaOCl was particularly difficult to control. Nevertheless it was possible to obtain a good yield (90%) of glucaric acid under very specific conditions (including a pH of 11.7 and the necessary presence of sodium bromide NaBr).

Furthermore, this document shows that, depending on the number of equivalents of NaOCl employed, the glucaric acid synthesis results in the preferential coproduction:

either of gluconic acid, i.e. of the monocarboxylic acid corresponding to glucaric acid, or of other dicarboxylic acids but which are small, namely tartaric acid and oxalic acid.

The authors believe that the coproduction of these last two acids is due to the oxidative decomposition of the monosaccharide (glucose, sorbitol) at two breakdown on the molecule, namely a) between the C-4 and C-5 carbon atoms and b) between the C-2 and C-3 carbon atoms.

More recently still, other pathways for the decomposition of glucaric acid have been suggested, as an attempt to explain the coproduction of meso-tartaric acid or of D-tartaric acid during the oxidation of glucose to glucaric acid in the presence of NaOCl, NaBr and TEMPO.

These decomposition pathways, hypothetical or otherwise, are described in the very recent paper by M. Ibert et al. entitled "Determination of the side-products formed during the nitroxide-mediated bleach oxidation of glucose to glucaric acid", Carbohydrate Research, 337 (2002), pp. 1059-1063.

In any case, in view of the above there is a number of drawbacks in the preparation of dicarboxylic acid, such as glucaric acid, from a monosaccharide, such as glucose, which may be optionally hydrogenated (sorbitol), and in particular:

- the use of sodium hypochlorite, which is not desirable because of the current restrictions for the protection of human life and the environment,
- the possible use of NaBr, that is not desirable given its capacity to generate halogenated entities,
- the need to closely monitor and control the reaction parameters, such as the pH and the concentration of NaOCl, in order to obtain a minimum or acceptable yield of desired product,
- the significant and undesired coproduction either of not profitable materials (NaCl) or monocarboxylic materials (gluconic acid and its salts) or dicarboxylic materials (oxalic and tartaric acids and their salts). These materials have a (very) greatly reduced molecular weight due to decomposition. They also have few (tartaric acid) or no (oxalic acid) OH groups. The presence of these materials reduces the properties, in particular the chelating or sequestering properties, of the glucaric acid composition.

In addition to these problems regarding the generation of decomposition products, the oxidation of mono-saccharides with TEMPO and sodium hypochlorite does not make it possible to obtain materials having three carboxylic functional groups, as is the case, with polycarboxylates commonly used in industry, such as citric acid and citrates.

SUMMARY OF THE INVENTION

Therefore there is a need for a means capable of eliminating the abovementioned disadvantages and in particular a means which, starting from monosaccharides, makes it possible a) to efficiently prepare compositions having a high content of polycarboxylic materials and in particular a high content of dicarboxylic materials, such as glucaric acid and its salts, and b) optionally to have novel compositions based on dicarboxylic materials and tricarboxylic materials. All these compositions are able to be advantageously used in the industries and for the purposes mentioned previously.

Thanks to the present invention, there will be no need to use sodium hypochlorite and to rigorously control the pH of the reaction.

MORE DETAILED DESCRIPTION

After numerous research studies, it is to the credit of the Applicant to have found, that such a means consists in using a specific method, i.e. an electrochemical oxidation treatment, carried out under specific conditions, in particular related to the specific nature of the anode used for the oxidation.

More specifically, a subject matter of the present invention is a method for preparing a polycarboxylic composition, characterized in that it comprises a stage in which a monosaccharide composition undergoes an electrochemical oxidation treatment carried out in the absence of sodium hypochlorite and in the presence a) of an amine oxide and b) of a carbon-based anode.

The term "polycarboxylic composition", within the meaning of the present invention, is understood as any composition comprising at least 50% by weight of one or more products chosen from the group consisting of dicarboxylic acids, tricarboxylic acids and the salts and the derivatives of said acids, this percentage being expressed as total dry weight of this (these) product(s) with respect to the total dry weight of said composition.

The term "monosaccharide composition" is understood as any composition comprising at least 50% by weight of one or more monosaccharide(s), this percentage being expressed as total dry weight of monosaccharide(s) with respect to the total dry weight of said composition.

This percentage can advantageously be at least 80% and can reach 100%.

The dry matter content of the monosaccharide composition can be within a very wide range, preferably between 0.1 and 50%, depending on possible economic or technical limitations, such as the optimization of the viscosity and the thermal characteristics of the reaction medium.

This dry matter (DM) can comprise at least one monosaccharide chosen from the group consisting of aldoses, ketoses and their respective derivatives, with the exception of those in which the hemiacetal functional group carried by the carbon in the position 1 (C1) has been protected against oxidation by amination, esterification, etherification, acetalization or grafting. Such "protected" derivatives at C1, which cannot be used as "monosaccharides" in the context of the present invention, consist, for example, of methyl α-glucopyranoside, isopropyl α,β-D-glucopyranoside, α-D-glucose pentaacetate or α,β-D-glucopyranosyl phosphate. The electrochemical oxidation of such derivatives generates uronic acids, i.e. monocarboxylic materials that only have oxidized the primary alcohol functional group carried by the carbon C6 of the glucose.

The production of such uronic acids by electrochemical oxidation of monosaccharides is widely described in the literature and in patent EP 1 027 931 and the following papers:

- "Catalytic oxidation of sugars by 4-(acetylamino)-TEMPO", K. Ito et al., Proc. Electrochem. Soc., 1993, Vol. 93-11, pp. 260-267,
- "Electroorganic Synthesis 66: Selective Anodic Oxidation of Carbohydrates Mediated by TEMPO", K. Schnatbaum et al., Synthesis, 1999, No. 5, pp. 864-872.

In the context of the present invention, any constituent of the monosaccharide composition that undergoes an electrochemical oxidation stage can be chosen from the group consisting of:

- aldohexoses, such as glucose, mannose, galactose or gulose,
- aldopentoses and aldotetroses, such as ribose, arabinose, xylose, erythrose and threose,
- ketoses, such as fructose, tagatose, sorbose and xylulose,
- the monosaccharides resulting from the hydrogenation of the abovementioned products, such as sorbitol, mannitol, galactitol, xylitol, ribitol, arabitol, erythritol and threitol,
- the monosaccharides resulting from the oxidation of the abovementioned products, such as gluconic acid, ketogluconic acids, glucaric acid, galactonic acid, xylonic acid or arabinonic acid, and their corresponding lactones and salts,
- the other derivatives of the abovementioned products, provided that they are not "protected" at C1 in the way indicated above. It can be, for example, 3-methoxyglucose.

Despite not being favoured, the monosaccharide composition used as starting material in the invention can comprise low percentages of products other than monosaccharides, such as di-, oligo- and polysaccharides or their derivatives.

Preferably, the monosaccharide composition comprises at least 80% by weight (dry/dry) of monosaccharide(s). For instance, the compositions may comprise 100% by weight (dry/dry) of glucose or 100% by weight (dry/dry) of a mixture of glucose and of gluconic acid or one of its salts or 100% by weight (dry/dry) of 5-ketogluconic acid or 100% by weight (dry/dry) of sorbitol or of threitol.

The salts of oxidized monosaccharides, such as, sodium or potassium gluconates, ketogluconates or glucarates, increase the conductivity of the reaction medium and, thus replacing sodium bromide.

The term "amine oxide", is understood as any compound disclosed in patents EP 780 399, EP 798 310 or EP 1 027 931 and which can be used as oxidation catalysts.

The electrochemical oxidation treatment of the monosaccharide composition can be carried out in any way accessible to a person skilled in the art. Preferably, according to the general methods or some alternative disclosed in the abovementioned patent EP 1 027 931 and/or the abovementioned paper by K. Ito, as regards:
- the nature of the catalyst (amine oxide) employed, which can consist of TEMPO or derivatives of the latter, optionally absorbed in all or part on a support,
- the reaction temperature, which can be less than 30° C., preferably between 1 and 20° C.,
- the nature of the cathode of the electrooxidation device, which can be based on platinum, titanium, stainless steel or a carbon material.

According to an essential characteristic of the invention, the anode used for the oxidation of the monosaccharide composition is preferably based on a carbon material.

The term "carbon material" includes crystalline carbon, such as graphite, or amorphous carbon, such as charcoal and its activated forms. This material can be used in the form of rod(s), beads, plates, grids, felts or pads.

Furthermore, the catalyst (amine oxide) can, in all or part, be immobilized on, adsorbed on or absorbed on this actual material prior to the oxidation stage.

Advantageously, and in particular out of concern for productive output, this material has a high specific surface, i.e. at least equal to $0.10 \, m^2/g$, preferably at least equal to $0.20 \, m^2/g$. It can be, by way of examples, a granular active charcoal or carbon felt, such as that of "Norit AX 08" type.

More preferably, said material can have a specific surface at least equal to $0.25 \, m^2/g$.

Surprisingly and unexpectedly, the Applicant Company has found that, the use of a carbon-based anode in a system without sodium hypochlorite makes it possible to obtain high yields of dicarboxylic materials, such as glucaric acid and its salts, i.e. of greater than 50% and preferably of greater than 90%.

The result is noteworthy because these yields can be obtained within a relatively wide range of pH values, i.e. of between 11 and 14, thus including pH values equal to or greater than 12, which were never exemplified in the abovementioned prior art.

Alternatively, the electrochemical oxidation treatment is carried out at a pH of between 10 and 14, preferably of between 11.5 and 14.

More surprisingly, the method of the invention makes it possible to directly obtain, i.e. without a purification stage, polycarboxylic compositions which comprise significant contents of both dicarboxylic (for example, of glucaric acid and/or its salts) and tricarboxylic materials. The content of tricarboxylic materials can advantageously be of between 3 and 50% by weight (dry/dry).

According to an embodiment of the invention, the polycarboxylic composition obtained after the electrochemical oxidation of the monosaccharide composition comprises:
- from 30 to 90% of one or more products chosen from dicarboxylic acids and their salts, and
- from 3 to 50% of one or more products chosen from tricarboxylic acids and their salts, these percentages being expressed as dry weight with respect to the total dry weight of said composition.

To the knowledge of the Applicant Company, the production from monosaccharide compositions of these compositions, including the polycarboxylic compositions in which the dicarboxylic component is composed of glucaric acid and/or of its salts, has never been achieved or even described.

As all compositions obtained by the method of the invention, these compositions may be advantageously used as novel industrial products in the following industries: detergents and cleaning agents, water treatment, metal treatment, plant treatment, fiber treatment, in particular textile fibers or paper fibers, hydraulic binders, adhesives, founding, paints or leather. These compositions can also be used in the food, pharmaceutical or cosmetic industries.

Thanks to the method of the invention, it is possible to obtain from hexoses, polycarboxylic compositions that comprise, a compound of novel structure having three carboxylic functional groups and six carbon atoms, in the free acid form and/or in the form of (a) salt(s).

After lengthy research and analytical studies, the Applicant Company is suggesting to name "2-carboxy-2,3,4-trihydroxypentanedioic acid" the compound having the following general planar formula:

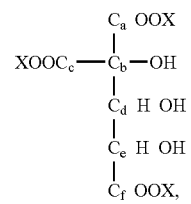

wherein:
- each of the 3 components "X" can be chosen from the group consisting of hydrogen, metals, preferably alkali metals and alkaline earth metals, amino groups, preferably the ammonium group, alkyl groups, preferably ethyl and methyl, and silyl groups, and
- each of the OH groups carried either by the carbon atom $C_d$ or by the carbon atom $C_e$ can lie either to the right or to the left of the carbon backbone.

According to the possible position of each of these two specific OH groups, this compound is disclosed for each of the four isomers (1), (2), (3) and (4) as described below (for which each component "X" is as defined above) and also for any mixture of at least any two of these isomers.

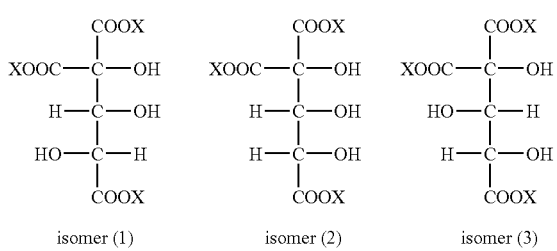

-continued

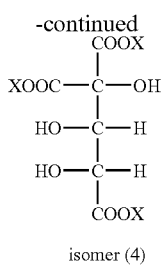

isomer (4)

Depending on the nature of the monosaccharide composition employed, the method of the invention makes it possible to obtain polycarboxylic compositions comprising:
  either only one of the four isomers described above, for example solely the isomer (1) when the monosaccharide composition is a D-galactose or D-5-ketogluconic acid composition or solely the isomer (2) when a D-fructose, D-mannose or D-2-ketogluconic acid composition is concerned,
  or a mixture in all proportions of at least two of the four isomers described above, for example a mixture predominantly comprising the isomer (1) and to a minor extent the isomer (2) when a D-glucose composition is concerned.

To the knowledge of the Applicant Company, none of these isomers has ever been synthesized, or even identified in the abovementioned prior art. Therefore, it should be emphasize that none of these isomers has ever been listed by Chemical Abstract Service (CAS) and thus does not have a "CAS" registration number.

Among the various ways of oxidating hexoses by chemical or electrochemical route, only the claimed method combining 1) the absence of NaOCl and 2) an electrochemical oxidation in the presence of a carbon-based anode can generate at least one of the isomers of 2-carboxy-2,3,4-trihydroxypentanedioic acid, in the free form, in the form of (a) salt(s) and/or in other forms.

The Applicant Company has not observed the formation of the acid or of its salts by substituting the anode with an anode based on other materials, in particular based on stainless steel.

The method of the invention makes it possible to obtain, with good yields, polycarboxylic compositions having high content of products which are simultaneously "overoxidized" (di- or tricarboxylated) and nondecomposed, i.e. comprising the same number of carbon atoms than that of the starting monosaccharide.

When applied to hexoses at a pH approximately of between 12 and 13.5, the electrochemical oxidation treatment of the invention, makes it possible to directly obtain polycarboxylic compositions as described above for which the total content of glucaric acid (in the free acid form and/or its salts) and 2-carboxy-2,3,4-trihydroxypentanedioic acid (in the free acid form and/or in the form of salts) is at least equal to 90%, this percentage being expressed as total dry weight of said products with respect to the total dry weight of the composition.

When said method is carried out at a pH of approximately between 12-13.5, a portion of the gluconic acid, optionally used as a starting material but more generally obtained as an intermediate product from glucose, is first significantly and rapidly converted to glucaric acid before significantly but gradually (for example, in 15 hours) converted to 2-carboxy-2,3,4-trihydroxypentanedioic acid. This is probably achieved by successive rearrangements probably involving 5-ketoglu-conic and 2-ketogluconic acids as some of the intermediates and generating little or no decomposition products comprising from 2 to 5 carbon atoms.

In addition, it is noteworthy to record, as the Applicant Company has observed, that the effects or results generated by the method of the invention and disclosed above can be obtained both in the presence and in the absence of sodium bromide, which is a precursor of the cooxidizing agent. The use of sodium bromide is widely recommended in the prior art during the (electro)chemical oxidation treatment. However like NaOCl, it generates undesirable halogenated entities.

The present invention will be described in even more detail in the following examples which are in no way limiting.

EXAMPLE 1

170 ml of osmosed water (2 Mohm.cm), 20 g (0.099 mol) of D-glucose in the form of dextrose monohydrate and 80 mg (0.51 mol) of "TEMPO" (2,2,6,6-tetramethyl-piperidinyloxy) are introduced into an electrolysis reactor connected to a system for controling pH and temperature and equipped with an anode composed of a carbon felt with a thickness of 5 mm and a specific surface of 0.3 m$^2$/g, supplied by Carbone-Corrbine, and with a cathode based on stainless steel.

Electrolysis is carried out at constant intensity (600 mA), the temperature of the reaction medium being maintained between 2 and 5° C. and the pH being regulated at 12.2 using a 4M potassium hydroxide solution. The electrolysis voltage (between anode and cathode) varies from 5V at the beginning of electrolysis to 3V at the end of the reaction. Electrolysis is halted when the amount of electricity delivered corresponds to 125% of the theoretical amount necessary for the oxidation of the glucose to glucaric acid (6 mol of electrons per mole of glucose).

The composition obtained directly on conclusion of this electrochemical oxidation stage (hereinafter "Composition 1") is concentrated to 100 ml under vacuum and then brought to pH 3.8 by gradual addition of Amberlite IR-120 resin. The medium is stirred at ambient temperature for 1 hour.

The precipitated material and the resin are filtered off through a sintered glass funnel of porosity 4.

The resulting filtrate is brought to pH 9 by addition of 4M potassium hydroxide solution and evaporated to dryness under vacuum (*), and the residue is then dried under vacuum (*) at 50° C. 9.9 g of a white solid material (hereinafter "Composition 1A") are thus obtained.

The mixture of precipitated material and of resin is taken up in 60 ml of osmosed water (2 Mohm.cm) and its pH is brought to 9 by addition of 4M potassium hydroxide solution. The resin is subsequently removed by filtration under vacuum.

The resulting filtrate is evaporated to dryness under vacuum (*) and the residue is then dried under vacuum (*) at 50° C.

(*) under a pressure of 14 mm of mercury (14 mmHg)

21.5 g of a white solid material (hereinafter "Composition 1B") are thus obtained.

Compositions 1, 1A and 1B were analyzed by gas chromatography on a capillary column after persilylation. The entities are located by their retention time and are quantified by using an internal standard and reference compounds.

The structures and the identities of some entities were investigated using:
  mass spectrometry coupled to gas chromatography, several types of derivatives being used and electron impact mode or chemical ionization mode being employed, $^1$H and $^{13}$C nuclear magnetic resonance spectrometry.

The analytical techniques used were those described in the abovementioned paper by M. Ibert.

After numerous research studies and qualitative and quantitative analytical studies, the Applicant Company found that Composition 1B comprised by weight (dry/dry), approximately:

93.7% of potassium glucarate,
 0.3% of potassium gluconate,
 0.3% of potassium tartrate,
 0.3% of potassium tartronate,
 0.5% of potassium oxalate, and
 5.0% of a potassium salt of a hitherto unknown tricarboxylic acid (hereinafter "Product X").

For its part, Composition 1A comprised by weight (dry/dry), approximately:

65.2% of said Product X in its tripotassium salt form,
 18.2% of potassium glucarate,
 2.5% of potassium gluconate,
 2.4% of potassium tartrate,
 3.5% of potassium tartronate and
 8.2% of potassium oxalate.

For its part, Composition 1, obtained directly on conclusion of the electrochemical oxidation stage and therefore in no way purified, comprised in particular approximately 70% by weight (dry/dry) of potassium glucarate and 24% by weight (dry/dry) of said Product X in its tripotassium salt form.

After numerous other research studies, the Applicant Company succeeded in purifying the Product X present in Composition 1A.

Said composition, brought to a dry matter of 29%, was treated on a column of resin of "PCR 532" type in the H$^+$ form, then brought to pH 9 using a 2M potassium hydroxide solution and precipitated by employing a saturated calcium chloride solution. After filtration, the precipitate was again brought to its acid form by addition of resin of "CA 200" type until completely redissolved.

The resin was subsequently removed by filtration and the filtrate, brought to pH 9 using a 2M potassium hydroxide solution, was evaporated to dryness.

Product x ("2-carboxy-2,3,4-trihydroxypentanedioic acid") was thus completely purified, as it happens in the potassium tricarboxylate form.

Numerous additional analytical studies then made it possible to be able to observe that said Product X was in fact composed of a mixture predominantly comprising (>80% by weight, as dry/dry) the isomer (1) described above and comprising, as minor product (<20% by weight, dry/dry), the isomer (2) described above.

Furthermore, electrooxidation tests on D-glucose in the presence of TEMPO were carried out under the same conditions as those described above, apart from the fact that the anode based on carbon felt was substituted by an anode composed either of stainless steel rods or of a stainless steel pad.

Surprisingly and unexpectedly, it was observed, after electrolyzing under these conditions for 24 hours, that 1) the anode composed of stainless steel rods did not allow substantial conversion of the glucose, and
2) the anode composed of a stainless steel pad made possible a low conversion of the glucose, this conversion generating essentially decomposition products, such as oxalic and tartaric acids.

In any event, in both cases, the Applicant Company did not observe the formation of any isomer of 2-carboxy-2,3,4-trihydroxypentanedioic acid or of any salt of such a product.

EXAMPLE 2

Moreover, the Applicant Company tested the effectiveness of Composition 1A as detergency cobuilder in a compact powder formulation comprising 25% by weight of zeolites.

It was found that said Composition 1A could be used effectively here for its ability to reduce the precipitation of calcium and magnesium salts, this being the case both at 20° C. and at 40° C. or 60° C.

For this purpose, Composition 1A proved to be overall more effective, for example, than commercial synthetic complexing agents, such as sodium salts of iminodisuccinic acid ("IDS") or ethylenediaminedi-succinic acid ("EDDS").

In addition, it was observed that Composition 1A could, within the same compact detergent powder, be advantageously used in combination with other cobuilders, such as sodium tripolyphosphates or phosphonates. These combinations showed synergistic effects in terms of reduction in the precipitation of calcium and magnesium salts.

Furthermore, Composition 1A proved to be useful as stabilizing agent for hydrogen peroxide employed in the treatment of paper pulps. This arose because of its capacity to complex with copper, which is less able to decompose the hydrogen peroxide.

EXAMPLE 3

The tests of Example 3 were carried out according to the general specifications of example 1 with a) an excess amount of current of 20% at 600 mA and an electrolysis time of 6 h 30 were used and b) the reaction pH was varied between 11 and 13.5 in increments of a pH unit of 0.5.

For each reaction pH studied, the levels, expressed as % (dry/dry) and as product in the acid form, of the following 4 products were measured:

gluconic acid (hereinafter "Acid A"),
 glucaric acid (hereinafter "Acid B"),
 2-carboxy-2,3,4-trihydroxypentanedioic acid (hereinafter "Acid C"),
 oxalic acid (hereinafter "Acid D").

The results below were obtained, the figures after the decimal point being rounded up to the higher percent for those at least equal to 0.50 and being rounded down to the lower percent for those below 0.50.

|  | pH Level (%) | | | | | |
| --- | --- | --- | --- | --- | --- | --- |
|  | 11 | 11.5 | 12 | 12.5 | 13 | 13.5 |
| Acid A | 13 | 6 | 3 | 2 | 1 | 0 |
| Acid B | 57 | 68 | 77 | 76 | 78 | 82 |
| Acid C | 23 | 21 | 17 | 18 | 16 | 10 |
| Acid D | 4 | 2 | 1 | 2 | 3 | 2 |

Another series of tests was carried out under the same conditions as those described above apart from the fact that, in addition, sodium bromide (NaBr) was introduced into the starting reaction medium. The sodium bromide was present in an amount corresponding to 50% (dry/dry) of the amount of glucose employed.

Overall, over the pH range studied, the same amounts and the same changes in the respective levels of each of the four acids were obtained as those observed in the absence of NaBr.

In addition, a test carried out at a pH of 10.5 in the presence of NaBr made it possible to obtain a polycarboxylic composition comprising in particular approximately (dry/dry) 25% of gluconic acid (Acid A), 37% of glucaric acid (Acid B), 22% of 2-carboxy-2,3,4-trihydroxypentanedioic acid (Acid C) and 7% of oxalic acid (Acid D), the remainder being essentially composed of tartronic and tartaric acids.

These results show that the method of the invention makes it possible to obtain, starting from monosaccharide compositions, polycarboxylic compositions with high content of over-oxidized (di- or tricarboxylated) and nondecomposed products, in which:
- the total content (dry/dry) of glucaric acid is at least 50%, preferably at least 70%, and/or
- the content (dry/dry) of glucaric acid and of 2-carboxy-2,3,4-trihydroxypentanedioic acid is at least 80%, preferably at least 90%.

It is surprising to observe that such yields of overoxidized/nondecomposed products can be obtained within a relatively wide range of reaction pH values, i.e. between 11 and 14.

In addition, it is noteworthy to emphasize that, for pH values equal to or greater than 12, preferably of between 12 and 13.5, it is possible to obtain simultaneously a) a content of glucaric acid exceeding 75% (dry/dry), for example from 77 to 82%, and b) a total content of glucaric acid and 2-carboxy-2,3,4-trihydroxypentanedioic acid exceeding 90% (dry/dry), for example from 92 to 94%.

The same general observations were made when "TEMPO" was substituted by its derivatives, such as:
- 4-acetylamino-2,2,6,6-tetramethylpiperidinyloxy,
- 4-methoxy-2,2,6,6-tetramethylpiperidinyloxy,
- 2-hydroxymethyl-7,7,9,9-tetramethyl-1,4-dioxa-8-azaspiro[4.5]decan-8-oxy,
- 2-methoxymethyl-7,7,9,9-tetramethyl-1,4-dioxa-8-azaspiro[4.5]decan-8-oxy,
- 7,7,9,9-tetramethyl-1,4-dioxa-8-azaspiro[4.5]-decan-8-oxy.

The same general observations were made using a device of "Priam 1-2C" type, as sold by Socem-Elec, as electrochemical reactor.

Furthermore, additional tests targeted at substituting the D-glucose (hexose) by a pentose, as it happens D-xylose, D-arabinose or D-ribose, or by a tetrose, as it happens a hydrogenated tetrose, such as D,L-threitol, have confirmed the production of polycarboxylic compositions comprising:
- predominantly, the corresponding dicarboxylated/nondecomposed product, for example xylaric acid from D-xylose, and
- as minor product, a tricarboxylated but also nondecomposed product, i.e. thus comprising the same number of carbon atoms as the starting monosaccharide.

EXAMPLE 4

These tests were carried out according to the general specifications of example 1 apart from the fact that, in the present case, the D-glucose was substituted by various monosaccharide compositions.

The type or types of isomer of 2-carboxy-2,3,4-trihydroxypentanedioic acid obtained in the reaction medium after electrooxidation is/are given in the table below according to the component or components constituting the dry matter of the starting monosaccharide composition, it being understood that:
- "1" means the isomer (1) as described above,
- "2" means the isomer (2) as described above,
- "3" means the isomer (3) as described above,
- "4" means the isomer (4) as described above,
- by way of example, "1+2" means a mixture of "the isomer (1)" and of "the isomer (2)" as are described above,
- "Na" means "sodium",
- "K" means "potassium".

| Starting monosaccharide(s) | Isomer(s) obtained |
| --- | --- |
| D-Glucose | 1* + 2 |
| L-Glucose | 3* + 4 |
| D-Galactose | 1 + 3 |
| D-Mannose | 2 |
| D-Gulose | 3* + 4 |
| D-Fructose | 2 |
| D-Sorbitol | 1* + 2 |
| D-Mannitol | 2 |
| Na gluconate | 1* + 2 |
| K glucarate | 1* + 2 |
| Na 5-ketogluconate | 1 |
| Na 2-ketogluconate | 2 |
| D-Glucose/Na gluconate mixture | 1* + 2 |

*predominant isomer of the mixture of isomers

This table shows that the method of the invention makes it possible, to influence the content of each of the 4 isomers of 2-carboxy-2,3,4-trihydroxypentanedioic acid, by varying the nature of the starting monosaccharide composition.

It should be noted that, in the case of a monosaccharide composition based respectively on D- or L-galactose, polycarboxylic compositions are obtained, by employing the method of the invention, in which the isomer obtained (respectively isomer (1) or isomer (3) —cf. table above) can be easily separated from the dicarboxylic compound obtained in conjunction, because of the very low solubility in water of the dipotassium salt of galactaric acid (or mucic acid).

What is claimed is:

1. A polycarboxylic composition produced by subjecting a monosaccharide composition to an electrochemical oxidation treatment carried out in the absence of sodium hypochlorite and in the presence of a) an amine oxide and b) a carbon-based anode, wherein said polycarboxylic composition comprises:
   from 30 to 90% of glucaric acid, in the free acid form and/or in the form of (a) salt(s), and
   from 3 to 50% of 2-carboxy-2,3,4-trihydroxypentanedioic acid, in the free acid form and/or in the form of (a) salt(s).

2. A polycarboxylic composition produced by subjecting a monosaccharide composition to an electrochemical oxidation treatment carried out in the absence of sodium hypochlorite and in the presence of a) an amine oxide and b) a carbon-based anode, wherein said polycarboxylic composition comprises glucaric acid and 2-carboxy-2,3,4-trihydroxypentanedioic acid, and in total at least 90% of glucaric acid and of 2-carboxy-2,3,4-trihydroxypentanedioic acid, this percentage being expressed as total dry weight of said products with respect to the total dry weight of said composition.

3. A method for preparing the polycarboxylic composition according to claim 1, said method comprising subjecting a monosaccharide composition to an electrochemical oxidation treatment carried out in the absence of sodium hypochlorite and in the presence of a) an amine oxide and b) a carbon-based anode.

4. The method as claimed in claim 3, wherein said anode is based on a carbon material having a specific surface at least equal to $0.10 \, m^2/g$, preferably at least equal to $0.20 m^2/g$.

5. The method as claimed in claim 4, wherein said carbon material has a specific surface at least equal to $0.25 m^2/g$.

6. The method as claimed in claim 4, wherein said anode is selected from the group consisting of carbon felts and granular active charcoals.

7. The method as claimed in claim 3, wherein said electrochemical oxidation treatment is carried out at a pH of between 10 to 14.

8. The method as claimed in claim 7, wherein the pH is between 11.5 and 14.

9. The method as claimed in claim 8, wherein the pH is between 12 and 13.5.

10. The method as claimed in claim 3, wherein said electrochemical oxidation treatment is also carried out in the absence of sodium bromide.

* * * * *